United States Patent
Ootani et al.

(10) Patent No.: US 10,365,273 B2
(45) Date of Patent: Jul. 30, 2019

(54) FLUORESCENCE IMMUNOASSAY SENSOR CHIP AND FLUORESCENCE IMMUNOASSAY METHOD

(71) Applicant: Konica Minolta Inc., Tokyo (JP)

(72) Inventors: Makiko Ootani, Tokyo (JP); Tsuruki Tamura, Hino (JP); Shinichi Muramatsu, Kiyose (JP)

(73) Assignee: KONICA MINOLTA, INC., Tokyo (JP)

( * ) Notice: Subject to any disclaimer, the term of this patent is extended or adjusted under 35 U.S.C. 154(b) by 578 days.

(21) Appl. No.: 14/891,093

(22) PCT Filed: Jun. 5, 2014

(86) PCT No.: PCT/JP2014/064979
§ 371 (c)(1),
(2) Date: Nov. 13, 2015

(87) PCT Pub. No.: WO2014/196603
PCT Pub. Date: Dec. 11, 2014

(65) Prior Publication Data
US 2016/0123972 A1   May 5, 2016

(30) Foreign Application Priority Data
Jun. 6, 2013 (JP) ................. 2013-119797

(51) Int. Cl.
*G01N 21/64* (2006.01)
*G01N 33/543* (2006.01)

(52) U.S. Cl.
CPC ..... *G01N 33/54373* (2013.01); *G01N 21/648* (2013.01); *G01N 21/6428* (2013.01);
(Continued)

(58) Field of Classification Search
None
See application file for complete search history.

(56) References Cited

U.S. PATENT DOCUMENTS 6,222,619 B1 * 4/2001 Herron ............. G01N 33/54373
                                                356/317
6,268,125 B1 * 7/2001 Perkins ................ G01N 21/553
                                                356/317
(Continued)

FOREIGN PATENT DOCUMENTS

JP    H09292332 A    11/1997
JP    2001516879 A   10/2001
(Continued)

OTHER PUBLICATIONS

T. Reichlin, et al; Early diagnosis of myocardial infarction with sensitive cardiac troponin assays; The New England Journal of Medicine; vol. 361; No. 9; Aug. 2009; pp. 858-867.
(Continued)

*Primary Examiner* — Rebecca L Martinez
(74) *Attorney, Agent, or Firm* — Lucas & Mercanti, LLP (57) ABSTRACT

Provided is a fluorescence immunoassay sensor chip and a fluorescence immunoassay method, which are capable of measuring, at the same time, a marker requiring high sensitivity due to its low content in a sample solution and a marker not requiring high sensitivity due to its high content in a sample solution. The fluorescence immunoassay sensor chip for use in fluorescence immunoassay for detecting and measuring markers contained in a sample solution includes: a dielectric member; a metal thin film formed on part of a main surface of the dielectric member; a first sensor part formed in a predetermined position on the metal thin film; and a second sensor part directly formed in a predetermined position on the dielectric member, wherein a ligand immobilized in the first sensor part and a ligand immobilized in the second sensor part capture different types of markers.

17 Claims, 5 Drawing Sheets

(52) U.S. Cl.
CPC ............... *G01N 2021/6439* (2013.01); *G01N 2021/6441* (2013.01); *G01N 2201/061* (2013.01); *G01N 2333/4712* (2013.01); *G01N 2333/805* (2013.01); *G01N 2800/324* (2013.01)

(56) References Cited

U.S. PATENT DOCUMENTS

| | | | |
|---|---|---|---|
| 2012/0075441 A1* | 3/2012 | Lenhert | C12Q 1/001 348/61 |
| 2013/0078148 A1* | 3/2013 | Kaya | G01N 21/648 422/69 |
| 2014/0170024 A1* | 6/2014 | Fujimaki | G01N 21/553 422/69 |

FOREIGN PATENT DOCUMENTS

| | | | |
|---|---|---|---|
| JP | 2007163323 A | | 6/2007 |
| JP | 2012052917 A | | 3/2012 |
| WO | 99/14594 A1 | | 3/1999 |
| WO | 2012090759 A1 | | 7/2012 |

OTHER PUBLICATIONS

M. Uematsu, et al; Usefulness of sensitive cardiac troponin I measurement . . . ; Therapeutic Research; vol. 31; No. 7; 2010; pp. 968-971.

C. R. DeFilippi, et al; Association of serial measures of cardiac troponin T using a . . . ; JAMA; vol. 304; No. 22; Dec. 2010; pp. 2494-2502.

T. Keller, et al; Serial changes in highly sensitive troponin I assay and early diagnosis . . . ; JAMA; vol. 306; No. 24; Dec. 2011; pp. 2684-2693.

International Search Report dated Sep. 2, 2014 for PCT/JP2014/064979 and English translation.

Extended European Search Report dated Feb. 15, 2017 from corresponding European Application No./Patent No. 14806991.7-1554 / 3006921 PCT/JP2014064979; Applicant: Konica Minolta, Inc.; Total of 7 pages.

Jun Ren et al: "Increased detection of human cardiac troponin I by a decrease of nonspecific adsorption in diluted self-assembled monolayers", Applied Surface Science, Elsevier, Amsterdam, NL, vol. 258, No. 13, Jan. 30, 2012, pp. 5230-5237, XP028466183.

* cited by examiner

FLUORESCENCE IMMUNOASSAY SENSOR CHIP AND FLUORESCENCE IMMUNOASSAY METHOD

CROSS REFERENCE TO RELATED APPLICATION

This Application is a 371 of PCT/JP2014/064979 filed on Jun. 5, 2014 which, in turn, claimed the priority of Japanese Patent Application No. JP2013-119797 filed on Jun. 6, 2013, both applications are incorporated herein by reference.

TECHNICAL FIELD

The present invention relates to a fluorescence immunoassay sensor chip and a fluorescence immunoassay method, which are capable of detecting and measuring two or more markers contained in the same sample at the same time using one sensor chip.

BACKGROUND ART

Immunoassays for early detection of diseases or detection of potential risks are required to have higher sensitivity to detect and measure a minute amount of analyte contained in a sample.

As an example of a method for detecting and measuring a minute amount of analyte contained in a sample with high sensitivity, a measuring method using SPFS (Surface Plasmon-field enhanced Fluorescence Spectroscopy) is known.

Figure 5:
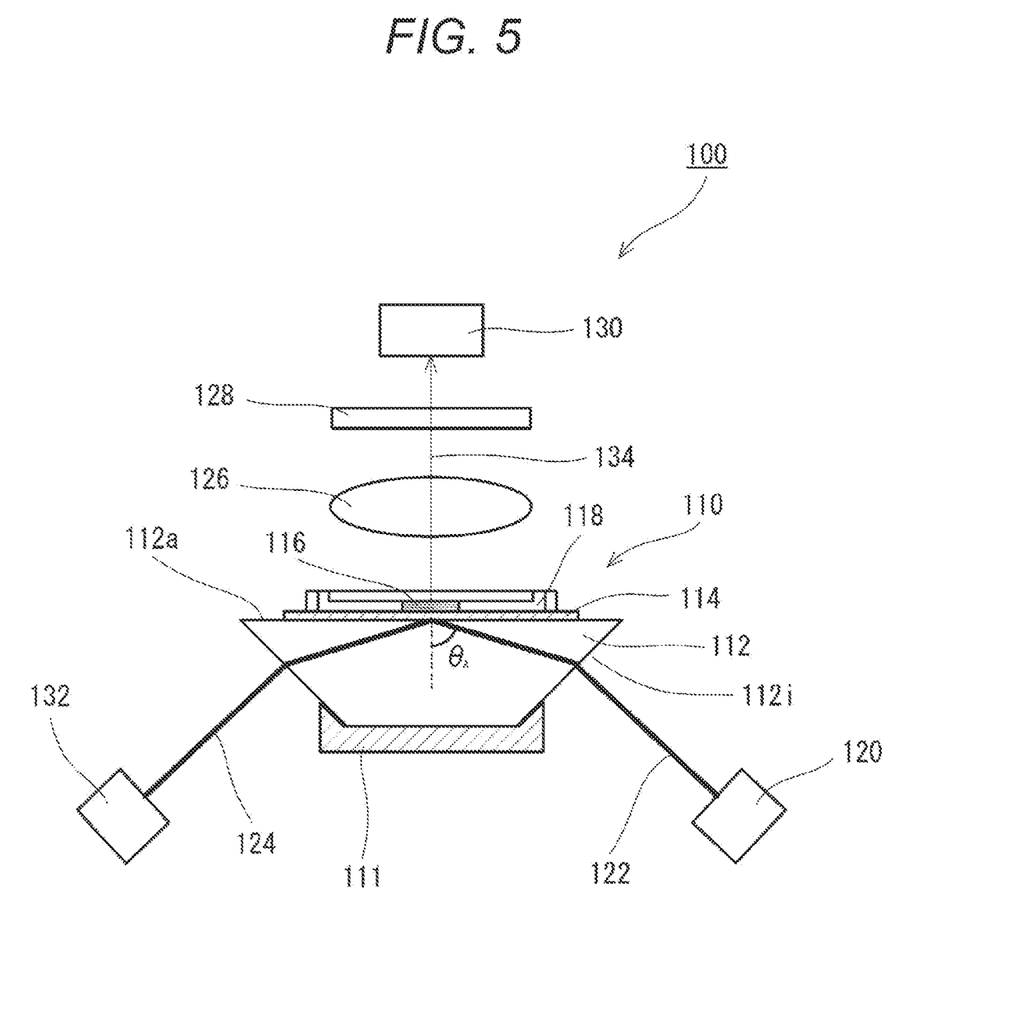
FIG. 5 is a schematic structural view for illustrating the structure of a conventional surface plasmon-field enhanced fluorescence spectroscopy apparatus (hereinafter, sometimes referred to as "SPFS apparatus").

FIG. 5 is a schematic structural view for illustrating the structure of a conventional surface plasmon-field enhanced fluorescence spectroscopy apparatus (hereinafter, sometimes referred to as "SPFS apparatus").

As shown in FIG. 5, a SPFS apparatus 100 comprises a sensor chip mounting part 111, and is configured so that a sensor chip 110 is mounted on this sensor chip mounting part 111.

The sensor chip 110 comprises a dielectric member 112 and a sensor part 116 formed by immobilizing a ligand in a predetermined position on a fine flow channel 118. The fine flow channel 118 is formed on a metal thin film 114 interposed between the fine flow channel 118 and a main surface 112a of the dielectric member 112.

On the dielectric member 112 side of the sensor chip 110 mounted on the sensor chip mounting part 111 of the SPFS apparatus 100, a light source 120 and a light-receiving means 132 are provided. The light source 120 emits excitation light 122 so that the excitation light 122 enters an incidence surface 112i of the dielectric member 112 and the sensor part 116 is irradiated with the excitation light 122 at a predetermined incident angle $\theta_A$ at which attenuated total reflection (ATR) occurs at the metal thin film 114. The light-receiving means 132 receives reflected light 124 that is light emitted from the light source 120 and reflected by the metal thin film 114.

On the other hand, a light-detecting means 130 is provided above the sensor chip 110. The light-detecting means 130 receives fluorescence 134 emitted from a fluorescent material labeling an analyte captured by the ligand immobilized in the sensor part 116.

It is to be noted that a light-collecting member 126 for efficiently collecting the fluorescence 134 and a wavelength-selecting functional member 128 are provided between the sensor chip 110 and the light-detecting means 130. The wavelength-selecting functional member 128 removes light other than the fluorescence 134 to selectively transmit only the fluorescence 134.

Such a SPFS apparatus 100 is used in the following manner.

First, a sample solution containing an analyte is introduced into the sensor part 116 through the fine flow channel 118, and then a fluorescent material for labeling the analyte is introduced through the fine flow channel 118 in the same manner to achieve a state where the analyte labeled with the fluorescent material is captured in the sensor part 116.

Then, in such a state, the light source 120 emits the excitation light 122 so that the excitation light 122 passes through the dielectric member 112 and the sensor part 116 is irradiated with the excitation light 122 at a predetermined incident angle $\theta_A$ at which attenuated total reflection occurs at the metal thin film 114. As a result, electric field enhanced by resonance between evanescent waves and surface plasmon from the metal thin film 114 is generated so that the fluorescence 134 from the fluorescent material captured in the sensor part 116 is efficiently excited.

Then, the excited fluorescence 134 is detected by the light-detecting means 130 to detect and measure a minute amount and/or very low concentration of the analyte.

Such an immunoassay apparatus is often used to measure a disease marker contained in the body fluid of a patient, such as blood, urine, or saliva. In this case, not a single marker but two or more related markers are generally measured to diagnose the disease state of the patient from the overall results of the measurements.

Therefore, Patent Literature 1 or 2 discloses that two or more markers are measured at the same time using one device, such as a flow cell or a sensor chip, by providing two or more sensor parts (assay regions) in the one device.

CITATION LIST

Patent Literatures

Patent Literature 1: JP 2001-516879 W
Patent Literature 2: WO 2012/090759 A

Non-Patent Literatures

Non-Patent Literature 1: N Engl J Med 2009; 361: 858-867
Non-Patent Literature 2: Therapeutic Research 2010; 31(7): 968-971
Non-Patent Literature 3: JAMA 2010; 304(22): 2494-2502
Non-Patent Literature 4: "Serial changes in highly sensitive troponin I assay and early diagnosis of myocardial infarction." JAMA. 2011 Dec. 28; 306(24):2684-93
Non-Patent Literature 5: "Study about usefulness of highly-sensitive cardiac troponin I assay in patients with chronic heart failure" Therapeutic Research Vol. 31 no. 7 2010

SUMMARY OF INVENTION

Technical Problem

For example, when a test for myocardial infarction is performed using such an immunoassay apparatus, myoglobin, creatine kinase MB, myosin light chain, troponin etc. are used as myocardial infarction markers.

Myoglobin is a low-molecular protein that is abundantly present in the cytoplasm of muscle cells, and therefore easily flows into blood from necrotic cardiomyocytes so that its abnormal value is detected within 1 to 3 hours after the onset of myocardial infarction. However, the myoglobin content of skeletal muscle is higher than that of cardiac muscle, and therefore the specificity of myoglobin for cardiac muscle is low. Although myoglobin is disadvantageous in that its specificity for cardiac muscle is low, the concentration of myoglobin can be easily and quickly measured, and therefore myoglobin is currently one of markers useful for early diagnosis of acute myocardial infarction and determination of success or failure of intravenous thrombolytic therapy.

Troponin is a protein complex present in thin filaments of myofibrils, and consists of three subunits, troponin T (molecular weight: 37000), troponin I (molecular weight: 22500), and troponin C (molecular weight: 18000). Troponin is released into blood from cardiomyocytes due to cardiomyocyte destruction caused by myocardial disease. In blood, the three subunits, troponin T, troponin I, and troponin C are present singly or form a complex of two or three different subunits.

Troponin I that is one of the subunits of troponin is hardly present in normal human blood, but is specifically present in the blood of humans with myocardial disease. Therefore, troponin I is known as a biomarker capable of early detecting myocardial disease. For example, Non-Patent Literature 4 describes the usefulness of highly sensitive troponin I in early diagnosis of acute myocardial infarction. Further, Non-Patent Literature 5 describes also the usefulness of highly sensitive cTnI assay in patients with chronic cardiac failure.

Troponin T is also very specific for cardiac muscle, and its abnormal value is detected over a long period of time from the early phase of myocardial infarction, which makes it possible to diagnose micromyocardial damage that cannot be detected by a conventional marker. That is, cTnT is useful in the diagnosis of myocardial infarction over a long period of time of 7 to 10 days from the early stage of myocardial infarction (from after 3 to 4 hours of the onset of myocardial infarction). A joint work team of the European Society of Cardiology and the American College of Cardiology changed diagnostic criteria for acute myocardial infarction in 2000 from diagnostic criteria based on electrocardiogram changes and clinical symptoms to new diagnostic criteria based on the blood level of cTnT or cTnI as well as electrocardiogram findings and clinical symptoms. In 2007, National Academy of Clinical Biochemistry reported guidelines for biomarkers in acute coronary syndrome (ACS) and heart failure in Circulation (2007; 115: e356-e375). This report describes that the use of troponin measurement as diagnostic aid in the diagnosis of ACS is a class I, level of evidence A recommendation. Further, Non-Patent Literature 3 describes that a large clinical trial (n=4221) was performed to investigate a correlation between the incidence of cardiovascular events and the value of cTnT in older adults. The value of cTnT was measured by Roche Elecsys 2010, and the lower limit of cTnT was 3 pg/mL and the cutoff value of cTnT was 13.5 pg/mL. As a result, the incidence of cardiovascular events varies depending on the value of cTnT even when the value of cTnT is lower than the cutoff value, which suggests the significance of measurement of the value of cTnT in a low concentration range.

Patients can be accurately tested by detecting and measuring two or more such myocardial infarction markers to determine their disease status.

However, conventional immunoassay apparatuses are limited in the measurable range of marker concentration, and therefore cannot measure a marker, such as troponin, that requires high sensitivity due to its low content in a sample solution and a marker, such as myoglobin, that does not require high sensitivity due to its high content in a sample solution at the same time using the same sample.

Therefore, such conventional immunoassay apparatuses perform immunoassay for each marker by changing the dilution factor of a sample solution according to a measurement item or adjusting, when magnetic particles are used, the number of the magnetic particles according to an item, or by changing excitation light used to measure fluorescence or changing conditions for measuring light with a light-receiving device. However, the former case involves a problem that the burden on patients increases due to an increased amount of necessary sample. Further, the latter case also involves a problem that it takes time to stabilize the assay apparatus after changing conditions for measuring light, which increases the time required for immunoassay.

Under the circumstances, it is an object of the present invention to provide a fluorescence immunoassay sensor chip and a fluorescence immunoassay method, which are capable of measuring a marker requiring high sensitivity due to its low content in a sample solution and a marker not requiring high sensitivity due to its high content in a sample solution at the same time using the same sample.

Solution to Problem

In order to achieve at least one of the above objects, one aspect of the present invention is directed to a fluorescence immunoassay sensor chip for use in fluorescence immunoassay for detecting and measuring markers contained in a sample solution, comprising: a dielectric member; a metal thin film formed on part of a main surface of the dielectric member; a first sensor part formed in a predetermined position on the metal thin film; and a second sensor part directly formed in a predetermined position on the dielectric member, wherein a ligand immobilized in the first sensor part and a ligand immobilized in the second sensor part capture different types of markers.

Advantageous Effects of Invention

According to the present invention, a marker requiring high sensitivity due to its low content in a sample solution and a marker not requiring high sensitivity due to its high content in a sample solution can be measured at the same time using the same sample.

Further, two or more sensor parts that capture different types of markers are provided on one sensor chip so that a marker requiring high sensitivity is measured by SPFS and a marker not requiring high sensitivity is measured by near-field fluorescence measurement, which makes it possible to perform wide dynamic range fluorescence immunoassay.

DESCRIPTION OF EMBODIMENTS

Hereinbelow, embodiments (examples) of the present invention will be described in more detail based on the drawings.

Figure 1:
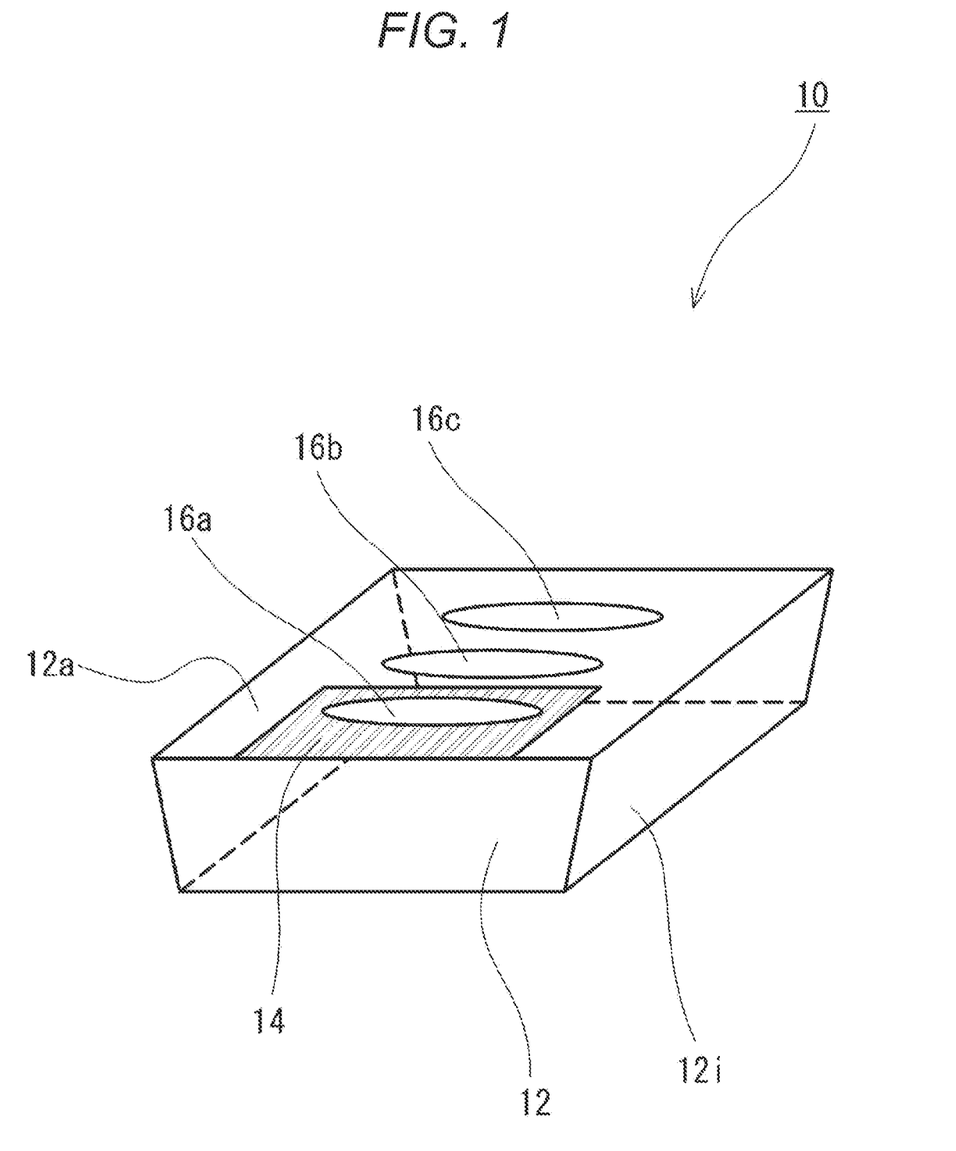
FIG. 1 is a schematic structural view for illustrating the structure of a sensor chip according to an embodiment of the present invention.
Figure 2:
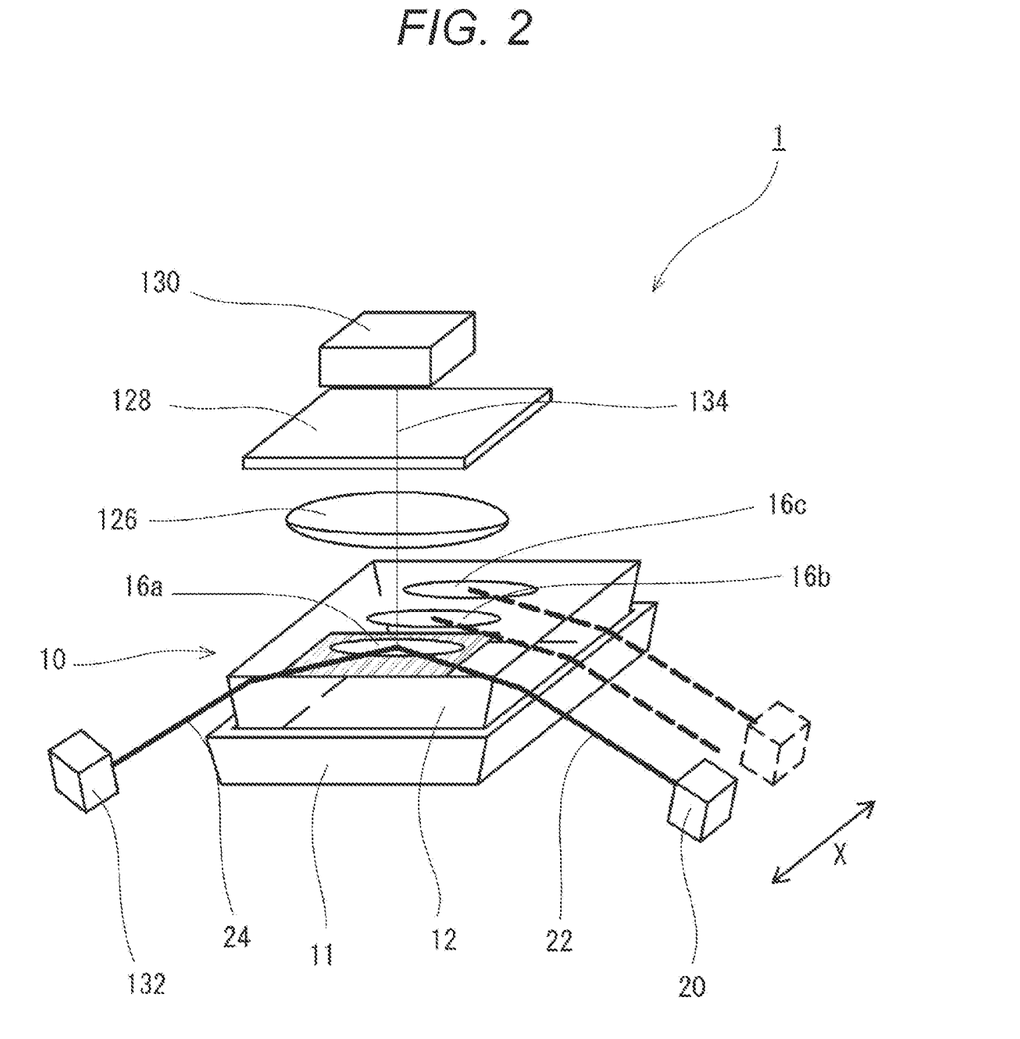
FIG. 2 is a schematic structural view for illustrating the structure of a fluorescence immunoassay apparatus on which the sensor chip shown in FIG. 1 is mounted to perform fluorescence immunoassay.

FIG. 1 is a schematic structural view for illustrating the structure of a sensor chip according to an embodiment of the present invention, and FIG. 2 is a schematic structural view for illustrating the structure of a fluorescence immunoassay apparatus on which the sensor chip shown in FIG. 1 is mounted to perform fluorescence immunoassay.

As shown in FIG. 1, a sensor chip 10 according to an embodiment of the present invention comprises a dielectric member 12, a metal thin film 14 formed on part of a main surface 12a of the dielectric member 12, a first sensor part 16a formed by immobilizing a ligand in a predetermined position on the metal thin film 14, and second sensor parts 16b and 16c each formed by directly immobilizing a ligand in a predetermined position on the dielectric member 12.

The area of each of the first sensor part 16a and the second sensor parts 16b and 16c is not particularly limited, but is preferably equal to or larger than that of a region to be irradiated with excitation light 22 that will be described later.

Particularly, in order to increase S/N during fluorescence immunoassay, the first sensor part 16a and the second sensor parts 16b and 16c preferably have the same shape as the region to be irradiated with the excitation light 22.

It is to be noted that each of the first sensor part 16a and the second sensor parts 16b and 16c has a well formed from a well member (not shown) to retain a sample solution added.

The ligand immobilized in the first sensor part 16a provided on the metal thin film 14 is a ligand for capturing a marker, such as troponin I, requiring high sensitivity. On the other hand, the ligand immobilized on each of the second sensor parts 16b and 16c provided on the dielectric member 12 is a ligand, such as myoglobin, for capturing a marker not requiring high sensitivity.

Such immobilization of ligands that capture different markers in the first sensor part and the second sensor parts allows the one sensor chip 10 to detect and measure two or more markers at the same time.

Further, as will be described later, wide dynamic range fluorescence immunoassay can be performed by performing SPFS measurement in the first sensor part 16a and near-field fluorescence measurement in the second sensor parts 16b and 16c.

Further, in this embodiment, as shown in FIG. 1, the dielectric member 12 is a hexahedron with a trapezoidal cross-section. The upper surface of the dielectric member 12 constitutes the main surface 12a described above, and one of the surfaces of the hexahedron constitutes an incidence plane 12i through which the excitation light 22 enters.

It is to be noted that the shape of the dielectric member 12 is not limited to the hexahedron described above. The dielectric member 12 shall be configured to have at least the main surface 12a on which the first sensor part 16a and the second sensor parts 16b and 16c are to be formed and the incidence plane 12i through which the excitation light 22 enters and to allow the excitation light 22 that has entered the incidence plane 12i to pass through the inside thereof so that the first sensor part 16a and the second sensor parts 16b and 16c are irradiated with the excitation light 22 at a predetermined incident angle θ at which total reflection occurs. For example, the dielectric member 12 may have a conical shape, a pyramid shape such as a triangular pyramid or a quadrangular pyramid, or a semi-cylindrical shape. Further, the dielectric member 12 may be configured to have two or more incidence planes 12i.

A material for forming the dielectric member 12 is not particularly limited as long as the material is optically transparent to at least excitation light. However, from the viewpoint of providing an inexpensive sensor chip excellent in handleability, the dielectric member 12 is preferably made of, for example, a resin material. When the dielectric member 12 is made of a resin material, examples of the resin material include: polyesters such as polyethylene terephthalate (PET) and polyethylene naphthalate; polyolefins such as polyethylene (PE) and polypropylene (PP); polycyclic olefins such as cyclic olefin copolymers (COC) and cyclic olefin polymers (COP); vinyl-based resins such as polyvinyl chloride and polyvinylidene chloride; polystyrene; polyether ether ketone (PEEK); polysulfone (PSF); polyether sulfone (PES); polycarbonate (PC); polyamide; polyimide; acrylic resins; and triacetyl cellulose (TAC).

A method for forming the dielectric member 12 is not particularly limited. However, for example, when such a resin material as described above is used, the dielectric member 12 can be formed by injection molding.

The metal thin film 14 can be made of the same metal as a metal thin film constituting a sensor chip used in a common SPFS apparatus. More specifically, the metal thin film 14 is preferably made of at least one metal selected from the group consisting of gold, silver, aluminum, copper, and platinum. Particularly, the metal thin film 14 is more preferably made of gold. These metals may be used in the form of an alloy or a metal laminate.

Each of the first sensor part 16a and the second sensor parts 16b and 16c is formed by immobilizing a ligand that specifically binds to a specific marker. A sample solution containing specific markers is added to the first sensor part 16a and the second sensor parts 16b and 16c, and then a fluorescent material for labeling the markers is added in the same manner to achieve a state where the markers labeled with the fluorescent material are immobilized in the first sensor part 16a and the second sensor parts 16b and 16c.

When used, the sensor chip 10 having such a structure as described above is mounted on a fluorescence immunoassay apparatus 1 as shown in FIG. 2.

As shown in FIG. 2, the fluorescence immunoassay apparatus 1 comprises at least a mounting part 11 for mounting the sensor chip 10 and a light source 20 for emitting the excitation light 22 toward the sensor chip 10 mounted on the mounting part 11.

The light source 20 is configured to be movable by a moving means (not shown) only in one axial direction indicated by an arrow X shown in FIG. 2 while being fixed at a predetermined elevation angle. It is to be noted that the one axial direction indicated by the arrow X refers to a direction parallel to the incidence plane 12i of the dielectric member 12.

It is to be noted that the fluorescence immunoassay apparatus 1 according to this embodiment is configured so that the light source 20 is movable, but may be configured so that the mounting part 11 having the sensor chip 10 mounted thereon is movable only in the one axial direction indicated by the arrow X. That is, the fluorescence immunoassay apparatus 1 shall be configured so that relative movement can occur between the light source 20 and the sensor chip 10.

It is to be noted that from the viewpoint of stabilizing measurement and reducing the production cost of the fluorescence immunoassay apparatus 1, moving an optical system such as the light source 20 is not preferred. Therefore, the fluorescence immunoassay apparatus 1 is preferably configured so that only the mounting part 11 having the sensor chip 10 mounted thereon is moved.

It is to be noted that other components of the fluorescence immunoassay apparatus 1 are the same as those of the conventional SPFS apparatus 100 described above. More specifically, the fluorescence immunoassay apparatus 1 comprises a light-receiving means 132 that receives reflected light 24 reflected by the main surface 12a of the dielectric member 12, a light-detecting means 130 that is provided above the sensor chip 10, and a light-collecting member 126 and a wavelength-selecting functional member 128 that are provided between the sensor chip 10 and the light-detecting means 130. Further, when the light source 20 is configured to be movable as described above, the light-detecting means 130 and the light-receiving means 132 shall also be configured to be movable so that fluorescence or the reflected light 24 can be received.

The fluorescence immunoassay apparatus 1 having such a structure as described above is basically used in the following manner as in the case of the conventional SPFS apparatus 100 described above.

First, a sample solution containing markers is added to the first sensor part 16a and the second sensor parts 16b and 16c, and then a fluorescent material for labeling the markers is added in the same manner to achieve a state where the markers labeled with the fluorescent material are immobilized in the first sensor part 16a and the second sensor parts 16b and 16c.

Then, in such a state, the first sensor part 16a formed on the metal thin film 14 is irradiated with the excitation light 22 emitted from the light source 20 and passed through the dielectric member 12 while the elevation angle of the light source 20 is changed in order. At this time, the reflected light 24 is received by the light-receiving means 132 to measure a change in its signal strength. By doing so, a predetermined incident angle θ is searched at which attenuated total reflection (ATR) occurs at the metal thin film 14 formed on the dielectric member 12.

Then, the excitation light 22 is passed through the inside of the dielectric member 12 to irradiate the first sensor part 16a with the excitation light 22 at the predetermined incident angle $θ_A$ so that evanescent waves enhanced by surface plasmon resonance are emitted from the surface of the metal thin film 14 to excite fluorescence of the fluorescent material immobilized in the first sensor part 16a.

Then, the fluorescence excited by the enhanced evanescent waves is detected by the light-detecting means 130, which makes it possible to detect and measure a marker requiring high sensitivity due to its low content in a sample solution.

That is, fluorescence immunoassay in the first sensor part 16a formed on the metal thin film 14 is performed by SPFS measurement, and therefore high-sensitivity marker detection can be performed.

Then, the light source 20 is moved to irradiate the second sensor part 16b with the excitation light 22 at the predetermined incident angle $θ_A$. As a result, evanescent waves are emitted from the main surface 12a of the dielectric member 12 so that fluorescence of the fluorescent material immobilized in the second sensor part 16b is excited.

Then, the fluorescence excited by the evanescent waves is detected by the light-detecting means 130, which makes it possible to detect and measure a marker not requiring high sensitivity due to its high content in a sample solution.

That is, fluorescence immunoassay in the second sensor part 16b formed on the dielectric member 12 is performed by near-field fluorescence measurement, and therefore marker detection not requiring high sensitivity can be performed.

Further, the light source 20 is moved to irradiate the second sensor part 16c with the excitation light 22 at the predetermined incident angle $θ_A$, which makes it possible to perform near-field fluorescence measurement as in the case of the second sensor part 16b.

The use of the sensor chip 10 having the first sensor part formed on the metal thin film 14 and the second sensor parts formed on the dielectric member 12 allows the fluorescence immunoassay apparatus 1 having a structure similar to that of the conventional SPFS apparatus to measure a marker requiring high sensitivity due to its low content in a sample solution and a marker not requiring high sensitivity due to its high content in a sample solution at the same time.

It is to be noted that in this embodiment, a predetermined incident angle $θ_A$ at which attenuated total reflection occurs is searched at the first sensor part 16a to perform SPFS measurement, and then the second sensor parts 16b and 16c are also irradiated with the excitation light at this incident angle $θ_A$, but the second sensor parts 16b and 16c where near-field fluorescence measurement is performed may be irradiated with the excitation light 22 at an incident angle at which total reflection of the excitation light 22 occurs.

More specifically, a predetermined incident angle θ at which total reflection occurs may be searched at the second sensor part 16c to irradiate the second sensor parts 16c and 16b in order with the excitation light 22 at this incident angle θ to perform near-field fluorescence measurement, and then a predetermined incident angle $θ_A$ at which attenuated total reflection occurs may be searched at the first sensor part 16a to irradiate the first sensor part 16a with the excitation light 22 at this incident angle $θ_A$ to perform SPFS measurement.

However, from the viewpoint of reducing measurement time, a search for the incident angle of the excitation light 22 is preferably performed in a short time, and therefore it is preferred that a predetermined incident angle $θ_A$ at which SPFS measurement can be performed is searched at the first sensor part 16a and fluorescence immunoassay is performed at this incident angle $θ_A$ in all the sensor parts.

Figure 3:
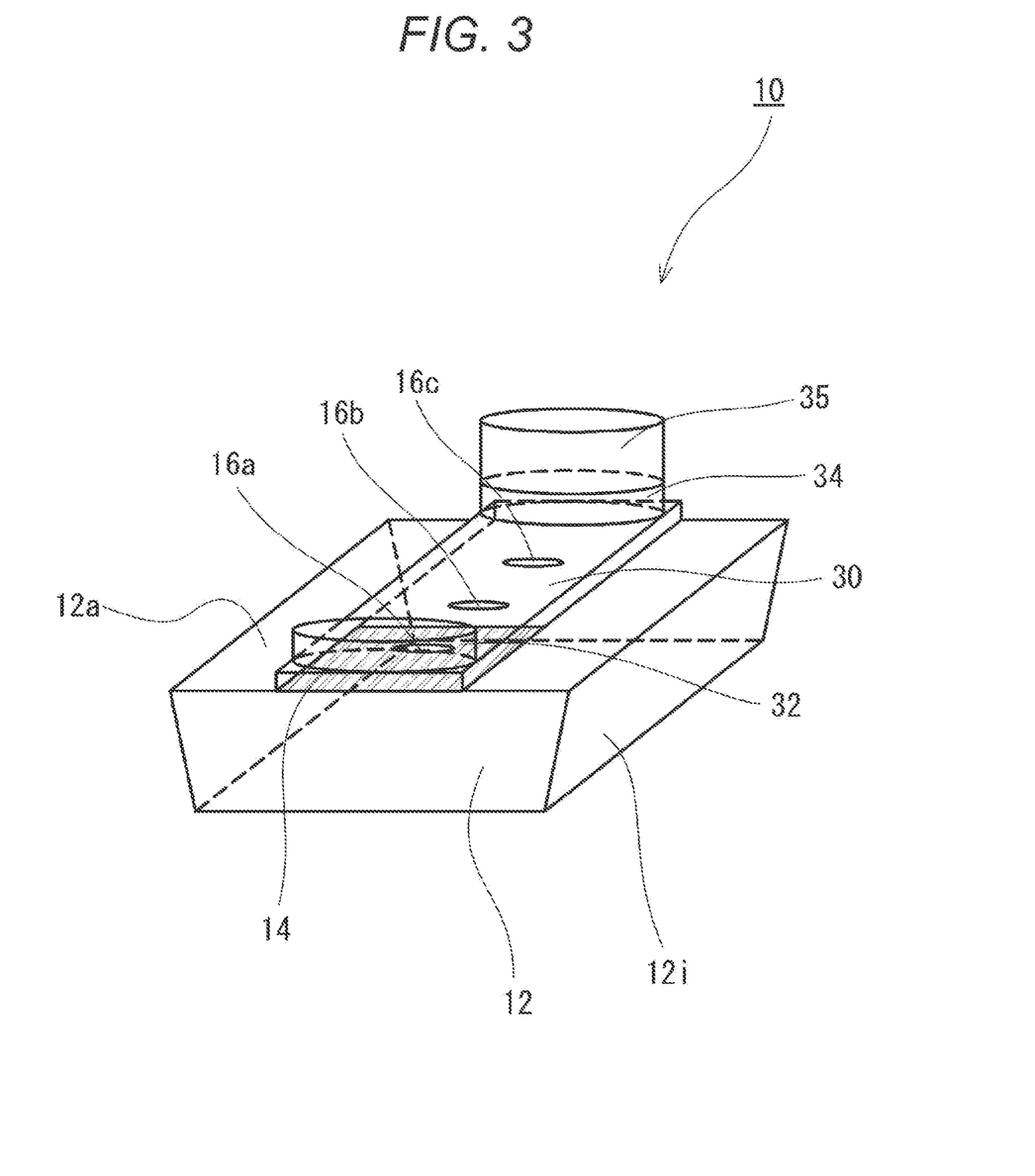
FIG. 3 is a schematic structural view for illustrating the structure of a sensor chip 10 according to another embodiment of the present invention.

FIG. 3 is a schematic structural view for illustrating the structure of a sensor chip 10 according to another embodiment of the present invention.

The sensor chip 10 according to this embodiment is basically the same in structure as the sensor chip 10 shown in FIG. 1, and therefore the same components are given the same reference numerals, and their detailed descriptions will not be repeated.

As shown in FIG. 3, this sensor chip 10 has a flow channel 30 formed on a dielectric member 12, and a first sensor part 16a and second sensor parts 16b and 16c are provided in the flow channel 30.

More specifically, the first sensor part 16a is formed by forming a metal thin film 14 in part of the flow channel 30 and immobilizing a ligand for capturing a marker requiring high sensitivity on the metal thin film 14.

Further, each of the second sensor parts 16b and 16c is formed by directly immobilizing a ligand for capturing a marker not requiring high sensitivity in the flow channel 30.

Further, in this embodiment, the flow channel 30 has a sample inlet 32 and a sample outlet 34, and the sample outlet 34 has a reservoir 35 in which a sample solution is temporarily retained.

When the sensor chip 10 having such a structure as described above is used, a sample solution is injected into the sample inlet 32 using, for example, a pipette and is repeatedly aspirated into and expelled from the pipette so that the sample solution is reciprocatingly moved between the pipette and the reservoir 35 through the first sensor part 16a and the second sensor parts 16b and 16c provided in the flow channel 30. As a result, markers contained in the sample solution are quickly and efficiently captured by the ligands immobilized in the first sensor part 16a and the second sensor parts 16b and 16c.

This makes it possible to reduce the amount of sample required for fluorescence immunoassay and therefore to reduce the burden on patients.

It is to be noted that in this embodiment, the reservoir 35 is provided to reciprocatingly feed a sample solution, but the sample inlet 32 and the sample outlet 34 may be connected to each other through, for example, a liquid circulating means (not shown) such as a pump to circulate a sample solution in one direction.

EXAMPLES

1. Measurable Range:

The concentrations of troponin I and myoglobin used as markers to be measured were changed in order and measured by SPFS measurement and near-field fluorescence measurement to determine the measurable concentration ranges of troponin I and myoglobin. The measurable ranges are shown in Table 1.

TABLE 1

| | Measuring method | |
|---|---|---|
| | SPFS measurement | Near-field fluorescence measurement |
| Troponin I | 0.003 ng/ml to 50.0 ng/ml | 2 ng/ml to 50.0 ng/ml |
| Myoglobin | 0.010 ng/ml to 100 ng/ml | 5 ng/ml to 1000 ng/ml |

It is known that sample solutions collected from patients contain troponin I at a low concentration, but contain myoglobin at a concentration higher than that of troponin I. As can be seen from this, it is preferred that troponin I is measured by SPFS and myoglobin is measured by near-field fluorescence measurement.

2. Relationship between Solution Feeding Condition and S/N:

S/N was measured under the condition where the sensor chip 10 shown in FIG. 1 was used in which a sample solution was allowed to stand for a predetermined time, or the sensor chip 10 shown in FIG. 3 was used in which a sample solution was passed through the flow channel 30 only once (one-pass feeding), or the sensor chip 10 shown in FIG. 3 was used in which a sample solution was passed through the flow channel 30 a predetermined number of times by reciprocating feeding.

It is to be noted that the S/N was calculated from a signal (S) and a noise (N) determined in the following manner using troponin I as a marker to be measured. A pooled serum of a patient with myocardial infarction was fed under each of the above solution feeding conditions, and then the amount of light measured by SPFS was detected by the light-detecting means 130 and regarded as the signal (S). On the other hand, a serum not containing troponin I was fed under each of the above solution feeding conditions, and then the amount of light measured by SPFS was detected by the light-detecting means 130 and regarded as the noise (N). The measurement results are shown in Table 2. It is to be noted that a washing process after feeding a sample solution and a labeling process in which troponin I was labeled with a fluorescent material were each performed under the same reaction conditions.

TABLE 2

| Solution feeding condition | S/N |
|---|---|
| One-pass feeding | 49 |
| Still-standing (Still-standing time: 3 min) | 60 |
| Still-standing (Still-standing time: 10 min) | 70 |
| Reciprocating feeding (Number of reciprocations: 10) | 80 |
| Reciprocating feeding (Number of reciprocations: 50) | 110 |
| Reciprocating feeding (Number of reciprocations:100) | 123 |

As show in Table 2, the S/N is higher when a sample solution is reciprocatingly fed, and the S/N increases as the number of reciprocations increases. That is, a sample solution is preferably reciprocatingly fed, and the number of reciprocations is preferably 50 or more.

3. Movement of optical system and sensor chip:

The variability of measurement results obtained when the sensor chip 10 was moved while an optical system (e.g., light source 20, light-detecting means 130) was fixed and the variability of measurement results obtained when the optical system was moved while the sensor chip 10 was fixed were determined.

It is to be noted that troponin I was used as a marker to be measured to calculate the coefficient of variation (CV). More specifically, the coefficient of variation was calculated by measuring serum samples different in the concentration of troponin I 10 times per sample by SPFS. The measurement results are shown in Table 3.

TABLE 3

| Sample No | Troponin I concentration (pg/mL) | CV in the case of moving sensor chip | CV in the case of moving optical system |
|---|---|---|---|
| 1 | 1.15 | 4.2 | 5.5 |
| 2 | 3.17 | 4.1 | 5.9 |
| 3 | 7.80 | 5.5 | 7.5 |
| 4 | 1.92 | 2.4 | 4.1 |
| 5 | 2.67 | 3.7 | 5.6 |

As can be seen from Table 3, the coefficient of variation is lower, that is, the stability of measurement is improved when the sensor chip is moved than when the optical system is moved.

4. Search for Incident Angle of Excitation Light:

Fluorescence immunoassay was performed using the sensor chip 10 shown in FIG. 1 by each method for searching the incident angle of excitation light shown in Table 4. It is to be noted that three sample solutions were subjected to fluorescence immunoassay, and troponin I and myoglobin were measured in the first sensor part 16a and the second sensor part 16b, respectively, and the amount of light measured in each of the sensor parts and detected by the light-detecting means 130 was regarded as a signal (S).

On the other hand, a sample solution containing neither troponin I nor myoglobin was subjected to fluorescence immunoassay, and the amount of light measured in each of the first sensor part 16a and the second sensor part 16b and detected by the light-detecting means 130 was regarded as a noise (N). The S/N was calculated from the signal (S) and the noise (N).

Further, the time required for measurement was defined as the time from the start of fluorescence immunoassay to the end of measurement in the first sensor part 16a and the second sensor part 16b, including the search time of incident angle of the excitation light 22. The measurement results are shown in Table 5.

TABLE 4

| | |
|---|---|
| A | A predetermined incident angle $\theta_A$ at which attenuated total reflection (ATR) occurs is searched in the first sensor part 16a, and SPFS measurement and near-field fluorescence measurement are performed at this incident angle $\theta_A$ in the first sensor part 16a and the second sensor part 16b, respectively. |
| B | A predetermined incident angle $\theta$ at which total reflection of the excitation light 22 occurs is searched in the second sensor part 16b, and SPFS measurement and near-field fluorescence measurement are performed at this incident angle $\theta$ in the first sensor part 16a and the second sensor part 16b, respectively. |
| C | A predetermined incident angle $\theta_A$ at which attenuated total reflection (ATR) occurs is searched in the first sensor part 16a and SPFS measurement is performed at this incident angle $\theta_A$ in the first sensor part 16a, and then a predetermined incident angle $\theta$ at which total reflection of the excitation light 22 occurs is searched in the second sensor part 16b and near-field fluorescence measurement is performed at this incident angle $\theta$ in the second sensor part 16b. |

TABLE 5

| Sample No. | Search method | S/N at the time of troponin I measurement | S/N at the time of myoglobin measurement | Time required for measurement (sec) |
|---|---|---|---|---|
| 1 | A | 33.5 | 13.8 | 27 |
|   | B | 27.3 | 13.3 | 27 |
|   | C | 33.5 | 13.3 | 70 |
| 2 | A | 17.3 | 5.1 | 27 |
|   | B | 13.3 | 4.6 | 27 |
|   | C | 17.3 | 4.6 | 70 |
| 3 | A | 5.2 | 2.0 | 27 |
|   | B | 3.9 | 1.9 | 27 |
|   | C | 5.2 | 1.9 | 70 |

As shown in Table 5, there was no significant difference in the S/N at the time of myoglobin measurement among the methods A to C. On the other hand, the S/N at the time of troponin I measurement was increased by searching the incident angle $\theta_A$ in the first sensor part 16a as in the case of the method A or C. Therefore, from the viewpoint of increasing the S/N, the incident angle of the excitation light 22 is preferably searched in the first sensor part 16a where SPFS measurement is performed.

Further, when a search for the incident angle of the excitation light 22 was performed twice as in the case of the method C, the time required for measurement was increased about 2.5 times as compared to when a search for the incident angle of the excitation light 22 was performed only once as in the case of the method A or B. Therefore, from the viewpoint of reducing the time required for measurement, a search for the incident angle of the excitation light 22 is preferably performed only once.

From these results, in order to increase the S/N of fluorescence immunoassay and reduce the time required for measurement, a search for the incident angle of the excitation light 22 is preferably performed only in the first sensor part 16a where SPFS measurement is performed as in the case of the method A described above.

Figure 4:
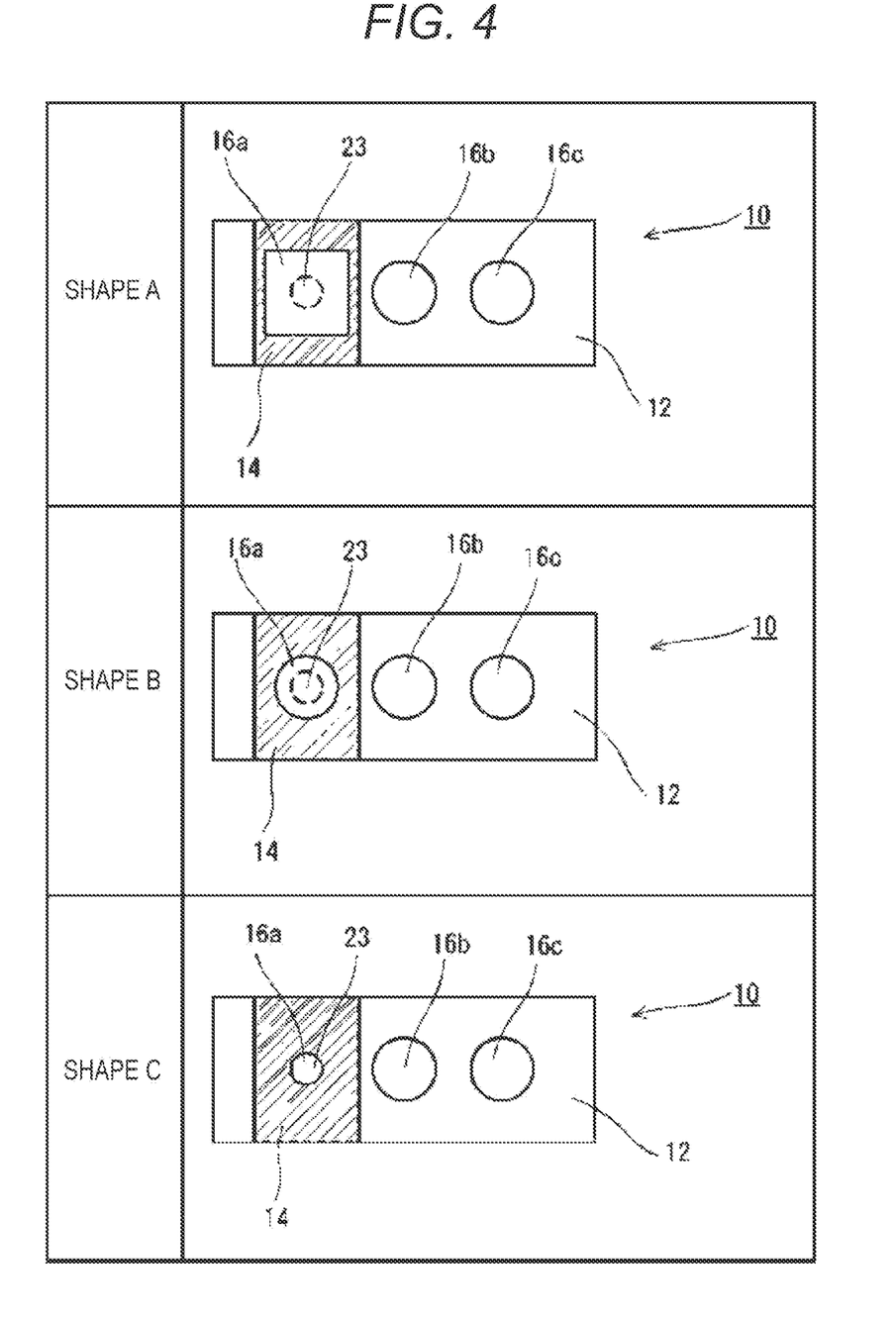
FIG. 4 is a schematic view for illustrating the patterns of combination of the shape of a first sensor part and the shape of a region to be irradiated with excitation light.

5. Shape of Sensor Part:

On the metal thin film 14 of the sensor chip 10, the first sensor part 16a was formed to have each shape shown in FIG. 4, and SPFS measurement was performed using the excitation light 22 having a circular cross-section with a diameter of 3 mm.

It is to be noted that the shapes A to C of the first sensor part 16a are a 8 mm×8 mm square, a circle with a diameter of 6 mm, and a circle with a diameter of 3 mm, respectively. It is to be noted that in FIG. 4, reference numeral 23 represents a region to be irradiated with the excitation light 22.

Further, S/N was calculated from a signal (S) and a noise (N). The signal (S) was determined by measuring troponin I as a marker and detecting the amount of light with the light-detecting means 130, and the noise (N) was determined by measuring a sample solution not containing troponin I in the same manner and detecting the amount of light with the light-detecting means 130. The measurement results are shown in Table 6.

TABLE 6

| Shape | S/N at the time of troponin I measurement |
|---|---|
| A | 57.8 |
| B | 80 |
| C | 222 |

As can be seen from Table 6, the S/N is increased by reducing the area of the first sensor part 16a to be close to the area of the region to be irradiated with the excitation light 22 or by making the shape of the first sensor part 16a close to that of the region to be irradiated with the excitation light 22.

This is because the marker is concentrated in the marker detection region, that is, in the region irradiated with the excitation light 22 so that the signal is enhanced.

Although the preferred embodiments of the present invention have been described above, the present invention is not limited thereto and various changes can be made without departing from the scope of the present invention. For example, the sensor chip 10 described above with reference to the embodiments has one first sensor part and two second sensor parts, but the number of the first sensor parts and the number of the second sensor parts are not limited and can be appropriately changed according to the number of types of markers that need to be measured at the same time.

REFERENCE SIGNS LIST

1 Fluorescence immunoassay apparatus
10 Sensor chip
11 Mounting part
12 Dielectric member
12a Main surface
12i Incidence plane
14 Metal thin film
16a First sensor part
16b Second sensor part
16c Second sensor part
20 Light source
22 Excitation light 24 Reflected light
30 Flow channel
32 Sample inlet
34 Sample outlet
35 Reservoir
100 SPFS apparatus
110 Sensor chip
111 Sensor chip mounting part
112 Dielectric member
112a Main surface
112i Incidence plane
114 Metal thin film
116 Sensor part
118 Fine flow channel
120 Light source
122 Excitation light
124 Reflected light
126 Light-collecting member
128 Wavelength-selecting functional member
130 Light-detecting means
132 Light-receiving means
134 Fluorescence

The invention claimed is:

1. A fluorescence immunoassay sensor chip for use in fluorescence immunoassay for detecting and/or measuring markers contained in a sample solution, comprising:
   a dielectric member having a main surface with a first part and a second part;
   a metal thin film formed on the first part of the main surface of the dielectric member and not present on the second part of the main surface;
   a first sensor part formed in a predetermined position on the metal thin film on the first part of the main surface; and
   a second sensor part formed in a predetermined position directly on the dielectric member on the second part of the main surface, wherein a ligand immobilized in the first sensor part and a ligand immobilized in the second sensor part capture different types of markers.

2. The fluorescence immunoassay sensor chip according to claim 1, wherein each of the first sensor part and the second sensor part has an area equal to or larger than that of a region on the main surface to be irradiated with excitation light.

3. The fluorescence immunoassay sensor chip according to claim 2, wherein each of the first sensor part and the second sensor part has the same shape as the region to be irradiated with the excitation light.

4. The fluorescence immunoassay sensor chip according to claim 1, wherein a flow channel is formed on the dielectric member, and wherein the first sensor part and the second sensor part are provided in the flow channel.

5. A fluorescence immunoassay method for detecting and/or measuring markers contained in a sample solution using the fluorescence immunoassay sensor chip according to claim 1, the method comprising:
   a dielectric providing step in which the dielectric member is provided, the dielectric member including the metal thin film formed on the first part of the main surface and not present on the second part of the main surface, the first sensor part formed on the first part of the main surface, and the second sensor part formed on the second part of the main surface;
   a marker capturing step in which the markers contained in the sample solution are labeled with a fluorescent material, and the first sensor part and the second sensor part are allowed to capture the markers;
   a first detection step in which a light source emits excitation light so that the excitation light passes through the dielectric member and the first sensor part is irradiated with the excitation light at a predetermined incident angle to detect fluorescence emitted from the fluorescent material labeling the marker captured in the first sensor part; and
   a second detection step in which the light source emits the excitation light so that the excitation light passes through the dielectric member and the second sensor part is irradiated with the excitation light at a predetermined incident angle to detect fluorescence emitted from the fluorescent material labeling the marker captured in the second sensor part.

6. The fluorescence immunoassay method according to claim 5, wherein after the first detection step, the sensor chip is moved while the light source is fixed to irradiate the second sensor part with the excitation light to perform the second detection step.

7. The fluorescence immunoassay method according to claim 5, wherein in the first detection step, the incident angle of the excitation light is an incident angle at which attenuated total reflection of the excitation light occurs at the metal thin film.

8. The fluorescence immunoassay method according to claim 7, wherein after the first detection step, relative movement between the sensor chip and the light source is caused while an elevation angle of the light source is fixed so that the incident angle of the excitation light becomes the incident angle at which attenuated total reflection occurs to irradiate the second sensor part with the excitation light to perform the second detection step.

9. A fluorescence immunoassay method for detecting and/or measuring markers contained in a sample solution using the fluorescence immunoassay sensor chip according to claim 4, the method comprising:
   a dielectric providing step in which the dielectric member is provided, the dielectric member including the metal thin film formed on the first part of the main surface and not present on the second part of the main surface, the first sensor part formed on the first part of the main surface, and the second sensor part formed on the second part of the main surface;
   a marker capturing step in which the markers contained in the sample solution are labeled with a fluorescent material, and the sample solution is injected into the flow channel to reciprocatingly move the sample solution through the first sensor part and the second sensor part to allow the first sensor part and the second sensor part to capture the markers;
   a first detection step in which a light source emits excitation light so that the excitation light passes through the dielectric member and the first sensor part is irradiated with the excitation light at a predetermined incident angle to detect fluorescence emitted from the fluorescent material labeling the marker captured in the first sensor part; and
   a second detection step in which the light source emits the excitation light so that the excitation light passes through the dielectric member and the second sensor part is irradiated with the excitation light at a predetermined incident angle to detect fluorescence emitted from the fluorescent material labeling the marker captured in the second sensor part.

10. The fluorescence immunoassay method according to claim 9, wherein after the first detection step, the sensor chip is moved while the light source is fixed to irradiate the second sensor part with the excitation light to perform the second detection step.

11. The fluorescence immunoassay method according to claim 9, wherein in the first detection step, the incident angle of the excitation light is an incident angle at which attenuated total reflection of the excitation light occurs at the metal thin film.

12. The fluorescence immunoassay method according to claim 11, wherein after the first detection step, relative movement between the sensor chip and the light source is caused while an elevation angle of the light source is fixed so that the incident angle of the excitation light becomes the incident angle at which attenuated total reflection occurs to irradiate the second sensor part with the excitation light to perform the second detection step.

13. The fluorescence immunoassay sensor chip according to claim 1, wherein the first sensor part has a square shape and the second sensor part has the circular shape.

14. The fluorescence immunoassay sensor chip according to claim 1, wherein each of the first sensor part and the second sensor part has circular shape that is equal to or larger than the region to be irradiated with the excitation light.

15. The fluorescence immunoassay sensor chip according to claim 14, wherein the first sensor part is smaller than the second sensor part.

16. The fluorescence immunoassay sensor chip according to claim 4, wherein the metal thin film is disposed closer to a sample inlet side of the flow channel than is the second sensor part.

17. The fluorescence immunoassay sensor chip according to claim 4, wherein the second sensor part is disposed downstream of the first sensor part in the flow channel.

* * * * *